United States Patent [19]

Kane et al.

[11] Patent Number: 4,952,593
[45] Date of Patent: Aug. 28, 1990

[54] 5-HETEROCYCLIC-2,4-DIALKYL-3H-1,2,4-TRIAZOLE-3-THIONES AND THEIR USE AS ANTIDEPRESSANTS

[75] Inventors: John M. Kane, Cincinnati; Francis P. Miller, Loveland, both of Ohio

[73] Assignee: Merrell Dow Pharmaceuticals Inc., Cincinnati, Ohio

[21] Appl. No.: 76,588

[22] Filed: Jul. 23, 1987

Related U.S. Application Data

[63] Continuation-in-part of Ser. No. 792,367, Oct. 29, 1985, abandoned.

[51] Int. Cl.$^5$ .................... A61K 31/34; A61K 31/38; A61K 31/41; C07D 249/12
[52] U.S. Cl. .................... 514/340; 514/307; 514/314; 514/384; 546/144; 546/167; 546/210; 546/276; 548/263.2
[58] Field of Search .............. 514/340, 314, 307, 384; 546/276, 172, 167, 148, 144, 210; 548/263, 265

[56] References Cited

U.S. PATENT DOCUMENTS

| | | | |
|---|---|---|---|
| 3,037,916 | 4/1962 | Goodman | 435/64 |
| 3,218,285 | 1/1966 | Suling et al. | 524/298 |

FOREIGN PATENT DOCUMENTS

| | | | |
|---|---|---|---|
| 865632 | 6/1978 | Belgium . | |
| 776118 | 5/1957 | United Kingdom | 546/276 |

OTHER PUBLICATIONS

Derwent Abst 79209e/38, Fuji KK, DE3203-661 9/16/82.
Xu et al; CA(103:104893e (1985).
Mazzone et al., CA(96):122698m (1982).
Kubota et al., CA 78:72014r (1973).
Russo et al, CA 77:126518h (1972).
Shutske et al., CA 95:219467c (1981).
Nath et al., 88:37708e.
D. H. Jones, et al., *J. Med. Chem.* 8(5), 676–680 (1965).
Chem. Abst. 57:1660(h), M. H. Shah, et al., *J. Sci. Ind. Res.* (India) 21C(3), 76–78 (1962).
M. Shah, et al., *J. Pharm. Sci.* 58(11), 1398–1401 (1969).
D. J. Brown and W. B. Cowden, *Aust. J. Chem.* 36(7), 1469–1475 (1983).
Chem. Abst. 93:46527a, S. M. El-Khawass, et al., *Sci. Pharm.* 47(4), 314–319 (1979).
H. L. Yale and S. S. Paila, *J. Med. Chem.* 9(1), 42–46 (1966).

*Primary Examiner*—Glennon H. Hollrah
*Assistant Examiner*—Peter G. O'Sullivan
*Attorney, Agent, or Firm*—Edlyn S. Simmons

[57] ABSTRACT

This invention relates to novel 5-$R_n$-(Het)-2,4-di alkyl-3H-1,2,4-triazole-3-thiones, to the intermediates and processes for their preparation, and to their use as antidepressants.

9 Claims, No Drawings

5-HETEROCYCLIC-2,4-DIALKYL-3H-1,2,4-TRIAZOLE-3-THIONES AND THEIR USE AS ANTIDEPRESSANTS

This is a continuation-in-part of application Ser. No. 792,367, filed Oct. 29, 1985, now abandoned.

This invention relates to 5-aryl-2,4-dialkyl-3H-1,2,4-triazole-3-thiones, to the intermediates and processes for their preparation, to their pharmacological properties, and to their use as antidepressants.

More specifically, this invention relates to compounds of the formula

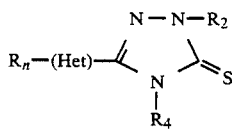

and the tautomers thereof, and the pharmaceutically acceptable salts thereof wherein R represents halogeno, $C_{1-6}$ lower alkyl, $C_{1-6}$ lower alkoxy, hydroxy, or trifluoromethyl, with n being zero, 1 or 2; each of $R_2$ and $R_4$ independently represents $C_{1-6}$ lower alkyl; and "Het" represents a heterocyclic moiety.

For R, halogeno preferably represents chloro or fluoro, and methyl and ethyl represent the preferred lower alkyl moieties, although all the straight, branched and cyclic manifestations thereof such as n-propyl, cyclopentyl, cyclohexyl and cyclopropyl are herein included. Lower alkoxy radicals include ethers having alkyl moieties of the $C_{1-6}$ alkyl group defined above. When n is one, representing a mono-substituted heterocyclic moiety, the R-substituent is located on any of the carbon atoms of the heterocyclic moiety. When di-substituted, the two R substituents are both located on a carbon atom of the heterocyclic moiety. The tautomeric forms are included for each of the compounds embraced within formula I. Preferably $R_2$ and $R_4$ each represents an alkyl group selected from methyl and ethyl, but may represent any straight or branched alkyl chain.

Representative of "Het" in formula I are such heterocyclic moieties as 2-, 3-, or 4-pyridyl, 2- or 3-furyl, 2- or 3-thienyl, 2- or 3- pyrrolyl, 6-isoquinolyl, 6-quinolyl and 3-quinolyl. Preferred is 4-pyridyl, with or without an R substituent, particularly when $R_n$ is a monochloro or monofluoro. State of the art salts formed with the heterocyclic moieties are generally employed, with the hydrochloride being one of convenience and general application. Such salts are formed by standard techniques well known in the art.

The compounds of formula I may readily be prepared using processes and procedures analogously known in the art as seen by the following reaction scheme.

REACTION SCHEME

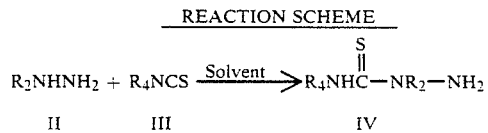

-continued
REACTION SCHEME

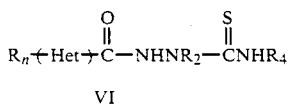

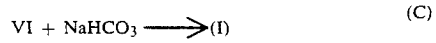

wherein $R_2$, $R_4$, and $R_n$-Het- are as previously defined.

In step A, the preparation of the thiosemicarbazides (IV) is readily effected by reacting hydrazine (II) with an isothiocyanate (III) by contacting the reactants in a suitable solvent. The reaction is quite rapid and may be carried out at 0° C. to room temperature. Although the reaction proceeds rapidly, the mixture may be left for up to 24 hours without significant decrease in yields. Reflux conditions may be employed but are not preferred Almost all solvents (with the exception of water and organic acids) may be used Anhydrous alcohols (preferably ethanol or methanol) are preferred although DMF, CHCl$_3$, CH$_2$Cl$_2$, THF and Et$_2$O may also be used. The required hydrazines and isothiocyanates are usually commercially available, but may be prepared by known techniques quite obvious to one of ordinary skill in the art.

In Step B, the desired substituted thiosemicarbazides (VI) may be prepared by reacting the thiosemicarbazides (IV) with an $R_n$-substituted-heterocyclic acid chloride (V) in an aprotic solvent such as pyridine, CHCl$_3$, THF and the like. The acylation proceeds rather easily at temperatures ranging from 0° C. to room temperature over periods of 3 to 24 hours, although elevated temperatures (e.g. reflux temperatures) may be employed Again, the acid halides (V) generally are commercially available but may also be prepared from the corresponding acids which are available from obvious starting materials.

In Step C, the substituted thiosemicarbazides (VI) are subjected to a cyclization reaction which is effected by heating the compounds (VI) in an aqueous base, e.g. sodium bicarbonate or sodium hydroxide. Alcoholic bases may be utilized, but generally are less desirable. The reaction is conducted at about the reflux temperature of the solvent, preferably at about 65°-100° C. In practice, the thiosemicarbazides (VI) need not be purified for use in Step C so that even 1:1 mixtures with pyridine hydrochloride, produced as a byproduct when pyridine is employed as a solvent in Step B, may be used.

The following specific examples are given to illustrate the preparation of the compounds of this invention although the scope of compounds exemplified is not meant to be limiting, this being so in view of the ease by which the compounds of formula I may be prepared.

Preparation of $R_2$,$R_4$-Substituted-Thiosemicarbazides

EXAMPLE 1

2,4-Dimethylthiosemicarbazide

To a stirred solution of methyl hydrazine (16.0 ml, $3.00 \times 10^{-1}$ mole) and sieve dry ethanol (50 ml) was added dropwise a solution of methyl isothiocyanate (22.0 g, $3.00 \times 10^{-1}$ mole) and sieve dry ethanol (30 ml). The reaction was exothermic and gently refluxed as the isothiocyanate was added. A precipitate soon formed. After stirring overnight, the reaction was cooled in an ice bath. The precipitate was then collected by filtration, washed with a little cold isopropanol, and dried by suction, affording a colorless solid: 26.7 g (75%). This material was crystallized two times from water and two times from isopropanol, affording small colorless needles: 14.7 g (41%), mp 135°–137° C.

Preparation of 1-($R_n$-Heterocyclyloyl)-$R_2$, $R_4$,
-Substituted Thiosemicarbazides

EXAMPLE 2

1-(4-Pyridoyl)-2,4-dimethylthiosemicarbazide

To a stirred solution of 2,4-dimethylthiosemicarbazide (6.7 g, $5.6 \times 10^{-2}$ mole) and pyridine (150 ml) was added dropwise 4-pyridoyl chloride HCl (10.0 g, $5.62 \times 10^{-2}$ mole). After stirring for 17 hours the solvent was evaporated to dryness, affording a mixture of the desired 1-(4-pyridoyl)-2,4-dimethylthiosemicarbazide and pyridine hydrochloride. In general, this mixture was used without further purification in the subsequent cyclization step. If pure 1-(4-pyridoyl)-2,4-dimethylthiosemicarbazide is desired, the above mixture is treated with water and that which does not dissolve is collected by filtration. After drying by suction this material is crystallized.

EXAMPLE 3

2,4-Dimethyl-1-(2-thienoyl)thiosemicarbazide

To a stirred, room temperature, solution of 2,4-dimethylthiosemicarbazide (3.75 g, $3.15 \times 10^{-2}$ mole) and pyridine (30 ml) was added dropwise 2-thiophenecarbonyl chloride (3.20 ml, $2.99 \times 10^{-2}$ mole). After stirring overnight the pyridine was evaporated at reduced pressure and the concentrate was treated with $H_2O$. The resulting semi-solid was extracted into ethyl acetate. The ethyl acetate extract was washed with saturated NaCl and subsequently dried over anhydrous $Na_2SO_4$. The drying agent was removed by filtration and the filtrate was evaporated at reduced pressure, leaving a slightly yellowish solid. This was treated with $Et_2O$ and the solid was collected by filtration affording a colorless powder: 4.7 g (68%), mp 176°–178° C.

Preparation of Final Products

EXAMPLE 4

5-(4-Pyridyl)-2,4-dimethyl-3H-1,2,4-triazole-3-thione

The 1:1 mixture from Example 2 and 1 molar aqueous $NaHCO_3$ (100 ml, $1.00 \times 10^{-1}$ mole) were stirred and warmed to reflux. After refluxing for 15 hours the reaction was allowed to cool in an ice bath. The resulting precipitate was collected by filtration and was dried by suction. The desired product was crystallized from ethyl acetate/hexane to yield large colorless plates: 4.1 g (35%), mp 150°–152° C.

EXAMPLE 5

2,4-Dimethyl-5-(2-thienyl)-3H-1,2,4-triazole-3-thione

A stirred mixture of 2,4-dimethyl-1-(2-thienoyl)thiosemicarbazide (4.7g, $2.0 \times 10^{-2}$ mole) and 1 molar aqueous $NaHCO_3$ (200 ml, $2.00 \times 10^{-2}$ mole) was heated to reflux for 6 hours. The reaction mixture was then placed in the refrigerator for several hours before the precipitate was collected by filtration. Crystallization from isopropanol afforded long colorless needles: 3.6 g (83%), mp 128°–129° C.

Other compounds embraced within formula I may similarly be prepared by using the procedures of Example 1–3 and substituting the appropriate Rn-heterocycloyl- and $R_2$, $R_4$-substituted reactants.

Using standard laboratory methodology, the pharmacological properties of the compounds, and their relative potencies, may readily be determined. When compared with other agents clinically known to be useful as antidepressants, the dosage regimen may readily be ascertained by those of ordinary skill in the art on the basis of the test results.

For example, the assay testing for prevention of reserpine-induced ptosis in mice and in rats is a standard assay. In those test groups, weighed mice or rats are housed individually in wire mesh stick cages and administered test compound or vehicle. At a selected time thereafter, reserpine, prepared as a 4 mg/ml solution in dilute acetic acid, is given to rats at a dose of 4 mg/kg subcutaneously, and to mice as a 0.2 mg/ml solution in dilute acetic acid at a dose of 2 mg/kg intravenously into a tail vein. In each assay the animals are examined individually in a plexiglass cylinder 90 minutes later in the rat assay or 60 minutes after administration of reserpine to mice. Prevention or delay of ptosis is considered significant if the average closure of both eyes is less than 50% after observing for 30 seconds. The $ED_{50}$ for prevention of ptosis is defined as the dose of test compound that significantly prevents ptosis in 50% of the test animals.

Another assay utilized to evaluate antidepressant activity is testing for the antagonism of RO-4-1284* -induced hypothermia. (*Niemegeers, Carlos, J. E. "Antagonism of Reserpine—Like Activity", edited by S. Fielding and H. Lal, published by Futura, pg. 73–98.) In this test, groups of male mice are weighed and housed individually in wire mesh stick cages. The rectal temperature of each mouse is recorded and the test compound or vehicle is then administered. At a selected time thereafter, RO-4-1284, prepared as a 2 mg/kg solution in distilled water, is administered at a dose of 20 mg/kg i.p. Mice are then placed in a cold room (36° F.) for 30 minutes, and then returned to room temperature for 30 minutes. At this time (60 minutes after RO-4-1284 administration) the rectal temperature of each mouse is again recorded. Under these conditions, RO-4-1284 causes a fall in rectal temperature of more than 6° C. The final temperatures of control groups of ten RO-4-1284-treated mice from a number of experiments are combined to form an "historic control" of 100 mice. This control is updated periodically by replacement of the oldest data. Any drugtreated animal which has final temperature (after RO-4-1284) which is greater than the mean +2 S.D. of the RO-4-1284 historic control is considered to exhibit significant antagonism to the hypothermic effect of RO-4-1284. The $ED_{50}$ for antagonism is defined as that dose of test compound which significantly antagonizes RO-4-1284 hypothermia in 50% of the test animals.

These standard laboratory tests demonstrate that the compounds of this invention have pharmacological effects generally attributed to anti-depressants and thus the compounds of this invention will elevate mood in patients suffering from depression and will have an end-use application in the treatment of patients suffering from endogenous depression, a term used interchangeably with psychotic or involutional depression. In this use, the compound (I) will exert a relatively quick onset of action and have a prolonged duration of activity. In general, the compounds may be expected to exert their antidepressant effects at dose levels of about 0.25–25 mg/kg of body weight per day although, of course, the degree of severity of the disease state, age of the patient and other factors determined by the attending diagnostician will influence the exact course and dosage regimen suitable for each patient. In general the parenterally administered doses are about ¼ to ½ that of the orally administered dose.

For oral administration, the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compounds of general formula I can be tableted with conventional tablet bases such as lactose, sucrose and cornstarch, in combination with binders, such as acacia, cornstarch or gelatin, disintegrating agents such as potato starch or alginic acid, and a lubricant such as stearic acid or magnesium stearate.

For parenteral administration, the compounds maybe administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthesic origin, for example, peanut oil, soybean oil and mineral oil. In general, water, saline, aqueous dextrose and related sugar solutions, ethanol, and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert material such as biodegradable polymers or synthetic silicones, for example Silastic ®, a silicone rubber manufactured by the Dow-Corning Corporation.

As is true in many classes of compounds with a pharmacological activity having a therapeutic end-use application, certain subgeneric groups and certain specific members of the class, because of their overall therapeutic index and their biochemical and pharmacological profile, are preferred. In this instance the preferred compounds are those wherein both $R_2$ and $R_4$ groups are methyl or ethyl, those wherein the Rn heterocyclic group is 4-, 3- or 2-pyridyl, or 2- or 3-thienyl.

We claim:

1. A compound of the formula

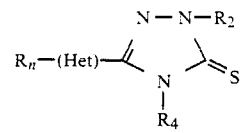

and the tautomers thereof, and the pharmaceutically acceptable salts thereof wherein
R is halogeno, $C_{1-6}$ lower alkyl, $C_{1-6}$ lower alkoxy, hydroxy or trifluoromethyl,
n is zero, 1 or 2,
$R_2$ and $R_4$ independently represent $C_{1-6}$ lower alkyl, and "Het" represents a heterocyclic moiety selected from the group consisting of 2-, 3- or 4-pyridyl, 2- or 3-furyl, 2- or 3-thienyl, 2- or 3-pyrrolyl, 6-isoquinolyl, 6-quinolyl and 3-quinolyl.

2. A compound of claim 1 wherein Rn-(Het)- is 2-, 3-, pyridyl.

3. A compound of the formula

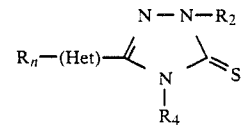

wherein
R is halogeno, $C_{1-6}$ lower alkyl, $C_{1-6}$ lower alkoxy, hydroxy or trifluoromethyl,
n is zero, 1 or 2,
$R_2$ and $R_4$ independently represent $C_{1-6}$ lower alkyl, and "Het" represents a heterocyclic moiety selected from the group consisting of 2- or 3-thienyl, and the tautomers thereof, or a pharmaceutically acceptable salt thereof.

4. A compound of claim 1 wherein each of $R_2$ and $R_4$ is methyl or ethyl.

5. A compound of claim 1 wherein each of $R_2$ and $R_4$ is methyl.

6. A compound of claim 1, said compound being 5-(4-pyridyl)-2,4-dimethyl-3H-1,2,4-triazole-3-thione.

7. A compound of claim 3, said compound being 5-(2-thienyl)-2,4-dimethyl-3H-1,2,4-triazole-3-thione.

8. A method of treating a patient in need of an antidepressant which comprises adminstering an effective amount of a compound of the formula

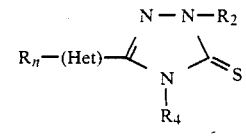

wherein
R is halogeno, $C_{1-6}$ lower alkyl, $C_{1-6}$ lower alkoxy, hydroxy or trifluoromethyl,
n is zero, 1 or 2,
$R_2$ and $R_4$ independently represent $C_{1-6}$ lower alkyl, and "Het" represents a heterocyclic moiety selected from the group consisting of 2-, 3- or 4-pyridyl, 2- or 3-furyl, 2- or 3-thienyl, 2- or 3-pyrrolyl, 6-isoquinolyl, 6-quinolyl and 3-quinolyl, and the tautomers thereof, or a pharmaceutically acceptable salt thereof.

9. A method of treating a patient in need of an antidepressent which comprises adminstering an effective amount of a compound of claim 3.

* * * * *

UNITED STATES PATENT AND TRADEMARK OFFICE
CERTIFICATE OF CORRECTION

PATENT NO. : 4,952,593

DATED : August 28, 1990

INVENTOR(S) : John M. Kane and Francis P. Miller

It is certified that error appears in the above-identified patent and that said Letters Patent is hereby corrected as shown below:

At Column 2, Line 40 patent reads "employed" and should read --employed.--

At Column 4, Line 54 patent reads "drugtreated" and should read --drug-treated--

At Column 5, Line 29 patent reads "maybe" and should read --may be--

At Column 5, Line 39 patent reads "synthesic" and should read --synthetic--

At Claim 2, Column 6, Line 18 patent reads "2-, 3-, pyridyl." and should read --2-,3-, or 4-pyridyl.--

Signed and Sealed this

Seventh Day of July, 1992

Attest:

DOUGLAS B. COMER

*Attesting Officer*   *Acting Commissioner of Patents and Trademarks*